United States Patent [19]
Miller et al.

[11] Patent Number: 6,031,158
[45] Date of Patent: Feb. 29, 2000

[54] PARTHENOCARPIC TRAIT IN SUMMER SQUASH

[75] Inventors: Christopher B. Miller, Yolo County, Calif.; Franco Vecchio, Fidenza, Italy

[73] Assignee: Pioneer Hi-Bred International, Inc., Des Moines, Iowa

[21] Appl. No.: 08/906,861

[22] Filed: Aug. 6, 1997

Related U.S. Application Data

[63] Continuation of application No. 08/587,050, Jan. 16, 1996, abandoned.

[51] Int. Cl.[7] .............................. A01H 5/00; A01H 5/02; A01H 5/08; C12N 5/04

[52] U.S. Cl. ........................... 800/310; 800/298; 435/410

[58] Field of Search ..................................... 800/200, 250, 800/DIG. 18, DIG. 21, 298, 310, 260; 47/58, DIG. 1; 435/410, 430

[56] References Cited

PUBLICATIONS

Nijs et al. Growth of parthenocarpic and seed–bearing fruits of zucchini squash. Cucurbit Genetics Cooperative. 6:84–85, 1983.

Rylski et al. Parthenocarpic fruit set and development in Cucurbitaceae and Solanaceae under protected cultivation in mild winter climate. Acta Horticulture. 287:117–126, 1990.

Chee. Initiation and maturation of somatic embroyos of squash (*Cucurbito pepo*) HortScience. 27:59–60, 1992.

*Primary Examiner*—Gary Benzion
*Assistant Examiner*—Melissa L. Kimball
*Attorney, Agent, or Firm*—Pioneer Hi-Bred International, Inc.

[57] ABSTRACT

Germplasm carrying a trait for parthenocarpy for the species *Cucurbita pepo*, particularly summer squash such as zucchini and related cultivars, and methods for selecting for the trait and transferring it to other germplasm are disclosed. A specific parthenocarpic hybrid of *Cucurbita pepo* is provided.

6 Claims, No Drawings

PARTHENOCARPIC TRAIT IN SUMMER SQUASH

This is a continuation of application Ser. No. 08/587,050 filed Jan. 16, 1996 now abandoned.

TECHNICAL FIELD

This invention relates to the production of hybrid vegetables, particularly hybrid summer squash such as zucchini and related cultivars.

BACKGROUND OF THE INVENTION

Most vegetable crops are hybridized. Separate male and female inbred lines are developed that are substantially homozygous. Each inbred parent makes its own genetic contribution to the hybrid offspring and the resulting plants exhibit heterosis, or hybrid vigor. The hybrid plants are typically larger and more vigorous, and produce more and/or larger fruit. However, since most vegetables are dicotyledonous, they are typically insect pollinated. Squash are generally pollinated by bees. During periods of cool weather, bee activity is reduced. In addition, in some production systems, such as greenhouse and tunnel production systems, large insect populations are not available for pollination. As a result of each of these circumstances, pollination suffers, with a consequent reduction in production of fruit.

In the past, numerous chemicals have been developed which have the effect of inducing parthenocarpy Parthenocarpic plants will set fruit without having first been pollinated. However, many of these chemicals are auxins (plant hormones) and all of them have other, unwanted, effects upon plants or upon the production environment.

Spontaneous parthenocarpy has occasionally been observed in plants. However, in most species this phenomenon does not occur reliably and reproducibly. Accordingly, a continuing need exists for natural, genetic systems for causing parthenocarpy to occur in vegetable crop plants.

DISCLOSURE OF THE INVENTION

The present invention relates to a reliable source of parthenocarpy for summer squash that allows breeding summer squash and screening their progeny to provide varieties that express a natural, genetically inherited trait of parthenocarpy. This invention allows the creation of both hybrid varieties and parent lines that, when crossed, produce hybrid offspring that exhibit pronounced parthenocarpy. It also includes new squash inbred lines and hybrids developed from these parental materials or their offspring, also exhibiting pronounced parthenocarpy.

The parthenocarpy shown by the plants and varieties of this invention appears to be multigenic and facultative. When these plants and varieties are pollinated, either by insect or by hand labor, fruit set and development occur normally. However, under conditions in which pollination is difficult or does not occur, these plants and varieties nevertheless set fruit that develops normally, whereas conventional plants and varieties of the prior art might not set fruit at all, or the fruit will set but will immediately begin to rot from the blossom end, and fruit development is poor at best, eventually being overtaken by the rot proceeding from the blossom end.

This invention also offers advantages in insect and disease control. Viral diseases of squash grown in the summer are generally transmitted by aphids. These insects can be controlled with the use of tissue nets, but such insect controls also prevent insect pollination. Thus, this invention would permit the isolation of a crop against aphids and aphid-transmitted viruses while also providing a normal fruit harvest, reducing the costs of insect and disease control without the use of chemical pesticides.

Original Source Materials

This invention originally resulted from evaluation of offspring of the cross of two lines of summer squash (*Cucurbita pepo*), one being a Dutch release known as "DG4" and the other being a public variety known as "Striata," "Striato" or "Striata d'Italia." DG4 is a very compact, bushy plant with dark leaves and very dark ("black"), short fruit. Striata is not a true variety but an ecotype consisting of several very similar varieties that are well adapted to the environment of Italy. The fruit are popular primarily in the Italian market for their coloration. Although it consists of several very similar varieties, the selection of subtypes within the ecotype has not been found to be critical and several successful crosses within a larger grouping of the ecotype have been performed. Striata varieties provide a plant with larger leaves and long fruit (15–20 cm at commercial size). The fruit have pronounced longitudinal stripes of lighter green on a very dark green background. Although Striata has generally poor characteristics and is not used in breeding or as a parent of commercial hybrids, the deposited hybrid, which conforms to the following description, can be used to transfer and propagate the parthenocarpic trait in any desired germplasm line of summer squash.

Parthenocarpic Hybrid

A hybrid of this invention has been made. Although parthenocarpy according to this invention shows dominant inheritance, the female was selected to have a parthenocarpic tendency. However, this tendency can only be determined by crossing with a parthenocarpic male of this invention. This is easily done in test crosses by performing the cross, and then observing for parthenocarpy.

The squash plant is made of a main stem, which grows first, and branches. The cotyledonary leaves (seed leaves) develop first, followed by the true leaves. Flowers develop in leaf axils and sex expression turns gradually from maleness to femaleness during plant growth. Thus, a flowering plant consists of 3 sequential phases of reproductive leaf axils: male, transitional (bearing both male and female flowers), and female. In a given environment, varieties differ quantitatively in sex expression—some are strongly male and others are strongly female or intermediate, depending on the relative length of their male and transitional phases. In a given environment, varieties also differ quantitatively in onset of flowering—some are early and others are late or intermediate depending, among other things, on the sequential position of the first reproductive leaf axil.

Numerous morphologic characteristics, corresponding to the "official" (PVP Office) description of the variety, have been measured for the hybrid. This hybrid summer squash of the species Cucurbia pepo produces a dark green cotyledon 60 mm. long and 25 mm. wide, with a rounded apex and plainly visible veining. The mature hybrid plant is of the glabrous bush type, with an average of 15 internodes on a round main stem 28 cm. in average length and 20 mm. diameter at the midpoint of the first internode. The plant has smooth reniform dark green leaves blotched with gray, averaging 34 cm. wide and 30 cm. long with shallow lobes and a flat, denticulate margin. Both leaf surfaces have soft hairs. The leaves are on petioles averaging 25 cm in length.

The hybrid is monoecious and has green-range pistillate flowers 4 cm in diameter with drumlike ovaries on pedicels averaging 2 cm. in length. The flowers have curved, frilled margins and sepals 1 mm wide and 7 mm long. The orange staminate flowers have sepals 2 mm wide and 40 mm. long on pedicels 4 cm. in length.

The hybrid shows good fruit set and elongation in the absence of pollination, even when additional hormones are not used. At market maturity, the fruit weighs on average 120 grams. It is elongate in shape with a rounded apex, a flattened base, and inconspicuous ribs with narrow, shallow rib furrows. The fruit surface is smooth and free from warts, with a slightly extended blossom scar button.

The rind of the fruit is soft and averages 1 mm in medial thickness. It has a regular coloration pattern with black-green stripes and some green spots on a dark green ground. The white flesh is 25 mm thick at the blossom end, 32 mm thick medially, and 30 mm thick at the stem end. It has a fine, firm, moist texture and a bland (insipid) flavor with excellent eating quality. The seed cavity conforms to the shape of the fruit, with abundant placental tissue and an inconspicuous central core.

The fruit is on straight, round, nontapered, untwisted stalks averaging 2 cm in length and 2 cm in diameter. The stalks have a smooth medium green surface with a hard texture, deep furrows and a slightly expanded attachment end that detaches easily.

The seeds are 14 mm long and 9 mm wide with a thickness of 3 mm. at maturity, with smooth, cream-color, dull face surfaces and curved, rounded margins. The average fruit provides 60 normal seeds that separate easily from the pulp and weigh 13 grams per 100 seeds.

This hybrid is susceptible to powdery mildew. It has not been tested against other common diseases. It has not been tested for susceptibility to squash bug, squash borer or other insects.

In comparison to other varieties, this hybrid is similar to the variety Narrow Bush for plant habit; to Black of Milano for fruit shape; to Consul for fruit color; and to any zucchini for culinary properties.

Breeding for Parthenocarpy

Selection for the parthenocarpic trait of this invention is a simple process. Plants of the parthenocarpic hybrid, seed of which has been deposited as ATCC Accession No._____, are grown to maturity with self-pollination to create an $F_2$ seed crop, which in turn is planted to grow a segregating population of plants. The size of the F2 generation of each cross should be as large as possible, considering cost and effective management. A reasonable estimate is 5000 plants. These plants are grown in isolation from insects and observed for parthenocarpy. This can be done in the open field by clipping the flowers of the forming fruit before they open to prevent pollination, and observing for parthenocarpy. As flowers appear on the plants, ordinary hair clips are applied to the flowers to keep them closed so that pollination cannot occur. Since zucchini mature to commercial size within a matter of a few days, the desired trait is readily observed within 2 to 3 days after clipping. Fruit of plants without the trait rot from the flower end within a few days. The same is true of plants in the greenhouse. However, since bees are not present in the greenhouse, pollination will not be provided and elongation will not occur in the absence of hormone treatments. The fruit will begin to degenerate rapidly. However, in successful parthenocarpic crosses, the fruit will elongate and reach commercial size even in the absence of pollination, even though insect pollination is prevented by greenhouse enclosure. The plants are observed for fruit development and elongation. Plants having the parthenocarpic trait will be observed to have normal fruit set and elongation, while plants lacking the parthenocarpic trait will have poor fruit set and poor fruit development with fruit rot occurring from the blossom end. Alternatively, the plants can be grown to seed maturity with all flowers clipped, and only the fruit that results from parthenocarpy will elongate and produce seed. The resulting parthenocarpic plants can be crossed to any desired germplasm and their offspring observed for the trait so that new parthenocarpic varieties can be developed.

Squash plants can be bred by both self-pollination and cross-pollination techniques. The development of a hybrid squash variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

The objective of commercial squash hybrid line development programs is to develop new inbred lines to produce hybrids that combine to produce desirable products having superior qualities.

The pedigree method of breeding is the mostly widely used methodology for new hybrid line development. In general terms this procedure consists of crossing two inbred lines to produce a non-segregating $F_1$ generation, and self pollination of the $F_1$ generation to produce the $F_2$ generation that segregates for all factors for which the inbred parents differ. Variations of this generalized pedigree method are used, but all these variations produce a segregating generation which contains a range of variation for the traits of interest.

Potentially monoecious plants of squash can be converted into female plants by a treatment with 2-chloroethylphosphonic acid (sold under several designations including Ethephon). The female plants can then be used for hybrid seed production. Alternatively, the method of U.S. Pat. No. 4,686,319, issued Aug. 11, 1987 to Shifriss, "Synthesis of genetic females and their use in hybrid seed production", the disclosures of which are hereby incorporated herein by reference, can be used.

Deposits

A deposit of the seed of the squash hybrid described herein is and has been maintained by Pioneer Hi-Bred International, Inc., 800, Capital Square, 400 Locust Street, Des Moines, Iowa, 50306-3453, since prior to the filing date of this application. Access to this deposit will be available during the pendency of the application to the Commissioner of Patents and Trademarks and any person determined by the Commissioner to be entitled thereto upon request. Upon allowance of any claims in the application, the Applicant(s) will make available to the public without restriction a deposit of at least 2500 seeds of the hybrid with the American Type Culture Collection (ATCC), 10801 University Boulevard, Manassas, Va. 20110. The seeds deposited with the ATCC will be taken from the same deposit maintained at Pioneer Hi-Bred and described above. Additionally, Applicant(s) will meet all the requirements of 37 C.F.R. §1.801 –1.809, including providing an indication of the viability of the sample when the deposit is made. This deposit of this hybrid will be maintained without restriction in the ATCC Depository, which is a public depository, for a period of 30 years, or 5 years after the most recent request, or for the effective life of the patent, whichever is longer, and will be replaced if it ever becomes nonviable during that period.

What is claimed is:

1. A squash plant of the species *Cucurbita pepo* selected from a population of progeny of the hybrid produced by crossing and DG4 and Striata having an inherited trait for parthenocarpy, or parts thereof.

2. A plant according to claim 1, selected from a population of progeny of the hybrid whose seeds have been deposited as ATCC Accession No. PTA-866.

3. A plant of a squash hybrid whose seeds have been deposited as ATCC Accession No. PTA-866.

4. A plant part according to claim 1 selected from the group consisting of roots, stems, leaves, cotyledons, flowers, fruit, embryos, pollen, and seeds.

5. Regenerable cells of a plant according to claim 1.

6. A culture of cells according to claim 5, capable of regenerating parthenocarpic squash plants.

* * * * *